(12) United States Patent
Estevez et al.

(10) Patent No.: US 10,416,306 B2
(45) Date of Patent: Sep. 17, 2019

(54) METHODS AND APPARATUS TO MEASURE AND ANALYZE VIBRATION SIGNATURES

(71) Applicant: Texas Instruments Incorporated, Dallas, TX (US)

(72) Inventors: Leonardo William Estevez, Rockwall, TX (US); Yuming Zhu, Plano, TX (US); Sujeet Milind Patole, Richardson, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 372 days.

(21) Appl. No.: 14/941,189

(22) Filed: Nov. 13, 2015

(65) Prior Publication Data

US 2017/0052148 A1 Feb. 23, 2017

Related U.S. Application Data

(60) Provisional application No. 62/205,821, filed on Aug. 17, 2015.

(51) Int. Cl.
*G01N 29/07* (2006.01)
*G01N 29/12* (2006.01)
(Continued)

(52) U.S. Cl.
CPC .............. *G01S 15/10* (2013.01); *G01N 29/07* (2013.01); *G01N 29/075* (2013.01); *G01N 29/11* (2013.01);
(Continued)

(58) Field of Classification Search
CPC ........ G01S 15/08; G01S 15/10; G01S 15/101; G01S 15/003; G01S 15/104; G01S 15/42;
(Continued)

(56) References Cited

U.S. PATENT DOCUMENTS 3,237,150 A * 2/1966 Beck ................. G01S 15/88
367/107
4,847,817 A * 7/1989 Au .................... G01S 7/539
367/135
(Continued)

OTHER PUBLICATIONS

Anderson, "Practical Techniques for Utilizing Ultrasonic Technology to Complement Vibration Analysis," P/PM Technology, vol. 14, Issue 1, Feb. 2001 (4 pages).
(Continued)

*Primary Examiner* — Natalie Huls
(74) *Attorney, Agent, or Firm* — Brian D. Graham; Charles A. Brill; Frank D. Cimino

(57) ABSTRACT

Methods and apparatus to measure and analyze vibration signatures are disclosed. In some examples, a meter is provided comprising a waveform generator to generate a waveform based on first distance measurements of an object. In some examples, the meter includes a waveform generator to determine a first vibration characteristic of the object based on the waveform. In some examples, the meter includes a comparator to compare the first vibration characteristic to a signature vibration characteristic of the object, the signature vibration characteristic of the object indicative of normal characteristics of the object. In some examples, the meter includes a reporter to, in response to determining the first vibration characteristic does not match the signature vibration characteristic, generate an alert.

25 Claims, 7 Drawing Sheets

(51) Int. Cl.
*G01N 29/11* (2006.01)
*G01N 29/14* (2006.01)
*G01S 15/10* (2006.01)
*G01S 7/539* (2006.01)
*G01S 15/58* (2006.01)
*G01S 15/00* (2006.01)

(52) U.S. Cl.
CPC ............ *G01N 29/12* (2013.01); *G01N 29/14* (2013.01); *G01S 7/539* (2013.01); *G01S 15/582* (2013.01); *G01N 2291/011* (2013.01); *G01N 2291/014* (2013.01); *G01N 2291/0258* (2013.01); *G01S 15/003* (2013.01)

(58) Field of Classification Search
CPC ........ G01S 15/50; G01S 15/52; G01S 15/582; G01S 15/586; G01S 15/62; G01S 15/878; G01S 15/8981; G01S 7/539; G01N 29/07; G01N 29/075; G01N 29/11; G01N 29/12; G01N 29/44; G01N 29/4409; G01N 29/4418; G01N 29/4427; G01N 29/4436; G01N 29/4454; G01N 29/449; G01N 29/46; G01N 2291/011; G01N 2291/014; G01N 2291/0258; G01N 29/14; G01N 29/30; G01N 29/045
See application file for complete search history.

(56) References Cited

U.S. PATENT DOCUMENTS

| | | | | |
|---|---|---|---|---|
| 4,849,741 A * | 7/1989 | Thomas | ............. | G05B 19/4065 340/680 |
| 4,922,467 A * | 5/1990 | Caulfield | ............... | G01V 1/001 367/135 |
| 5,672,825 A * | 9/1997 | Uno | ..................... | G01N 29/045 73/579 |
| 5,867,125 A * | 2/1999 | Cluff | ....................... | G01S 1/045 342/127 |
| 5,920,520 A * | 7/1999 | Gallagher | ............... | F41H 11/12 367/138 |
| 5,974,881 A * | 11/1999 | Donskoy | ................ | G01N 29/11 367/87 |
| 6,023,976 A * | 2/2000 | Borza | ..................... | F41H 11/12 73/598 |
| 6,109,112 A * | 8/2000 | Borza | ..................... | F41H 11/12 73/661 |
| 6,402,704 B1 * | 6/2002 | McMorrow | ...... | A61B 5/150221 600/576 |
| 6,561,031 B2 * | 5/2003 | Borza | ..................... | F41H 11/12 367/87 |
| 7,092,965 B2 * | 8/2006 | Easwar | ................. | H04N 19/40 |
| 9,043,182 B2 * | 5/2015 | Seo | .................... | G01B 9/02007 702/152 |
| 9,057,682 B2 * | 6/2015 | Nakayama | ................ | F01D 5/16 |
| 9,400,239 B2 * | 7/2016 | Lemaster | ................. | G01N 3/58 |
| 2008/0062151 A1 * | 3/2008 | Kent | ..................... | G06F 3/0418 345/177 |
| 2010/0117993 A1 * | 5/2010 | Kent | ..................... | G06F 3/0436 345/177 |
| 2010/0235137 A1 * | 9/2010 | Seo | .................... | G01B 9/02007 702/150 |
| 2011/0066390 A1 * | 3/2011 | Macleod | .................. | G01N 3/06 702/56 |
| 2011/0137588 A1 * | 6/2011 | Walker | ................... | G01N 29/07 702/56 |
| 2011/0261652 A1 * | 10/2011 | Horsky | ................ | B06B 1/0253 367/97 |
| 2012/0021873 A1 * | 1/2012 | Brunner | ............. | A63B 24/0075 482/9 |
| 2012/0172744 A1 * | 7/2012 | Kato | ..................... | A61B 5/0478 600/544 |
| 2013/0190584 A1 * | 7/2013 | Walker | ................. | A61B 5/0048 600/369 |
| 2013/0293586 A1 * | 11/2013 | Kaino | .................... | G08G 1/005 345/633 |
| 2013/0336093 A1 * | 12/2013 | Suvanto | .................. | G01S 15/06 367/99 |
| 2013/0345937 A1 * | 12/2013 | Strelioff | .............. | A01M 7/0057 701/50 |
| 2014/0367401 A1 * | 12/2014 | Stralin | .................... | A47K 10/22 221/6 |
| 2014/0378820 A1 * | 12/2014 | Gururaj | .................. | A61B 5/055 600/411 |
| 2015/0107361 A1 * | 4/2015 | Pirkle | ..................... | G01N 29/02 73/632 |
| 2015/0140534 A1 * | 5/2015 | Brunner | ............... | A63B 22/025 434/255 |
| 2015/0173652 A1 * | 6/2015 | Brunner | ............. | A63B 24/0087 482/7 |
| 2015/0276683 A1 * | 10/2015 | Bamberg | .............. | G01N 29/041 73/632 |
| 2016/0061597 A1 * | 3/2016 | De Bruijn | ............... | H04S 7/301 367/125 |
| 2016/0085725 A1 * | 3/2016 | Leonard | ............... | G06K 9/6272 702/189 |
| 2016/0178392 A1 * | 6/2016 | Goldfain | .............. | A61B 5/1123 702/104 |
| 2016/0178748 A1 * | 6/2016 | Shin | ........................ | G01S 15/42 367/99 |
| 2017/0059704 A1 * | 3/2017 | Xie | ......................... | G01S 15/93 |
| 2017/0090599 A1 * | 3/2017 | Kuboyama | ............. | G06F 3/038 |
| 2018/0074022 A1 * | 3/2018 | Huang | ................... | G01N 29/12 |

OTHER PUBLICATIONS

Digi-Key Electronics, "Slam Stick Vibration Recorder," 1995-2015, retrieved from <http://www.digikey.com/us/en/ph/mide/slamstick.html?WT.z_Tab_Cat=F . . . >, retrieved on Nov. 2, 2015 (1 page).
GTI Predictive Technology, "Ultrasonic Sensor for iPad—For Leak Detection and Testing Bearing Lubrication Overview," 2015, retrieved from <http://gtipredictive.com/ultrasonic/ . . . >, retrieved on Nov. 2, 2015 (1 page).

* cited by examiner

METHODS AND APPARATUS TO MEASURE AND ANALYZE VIBRATION SIGNATURES

RELATED APPLICATION

This patent claims the benefit of U.S. Provisional Application Ser. No. 62/205,821, which was filed on Aug. 17, 2015, and is hereby incorporated herein by reference in its entirety.

FIELD OF THE DISCLOSURE

This disclosure relates generally to object detection and measurement, and, more particularly, to methods and apparatus to measure and analyze vibration signatures.

BACKGROUND

In recent years, vibration analysis has been used to determine details about measured objects, such as, for example, faults or degradation, that would otherwise go undetected until an actual fault. Often, vibration analysis can detect defects preemptively, before the defects cause a major problem. To provide such vibration analysis, meters have been placed on objects to detect vibrations by allowing the meters to oscillate along with the objects. Additionally, probes have been used to detect ultrasonic sound waves emitted from objects and convert the ultrasonic waves into the audible and/or visual domain.

SUMMARY

Methods and apparatus to measure and analyze vibration signatures are disclosed. In some examples, a meter is provided comprising a waveform generator to generate a waveform based on first distance measurements of an object. In some examples, the meter includes a waveform generator to determine a first vibration characteristic of the object based on the waveform. In some examples, the meter includes a comparator to compare the first vibration characteristic to a signature vibration characteristic of the object, the signature vibration characteristic of the object indicative of normal characteristics of the object. In some examples, the meter includes a reporter to, in response to determining the first vibration characteristic does not match the signature vibration characteristic, generate an alert.

DETAILED DESCRIPTION

Figure 1A:
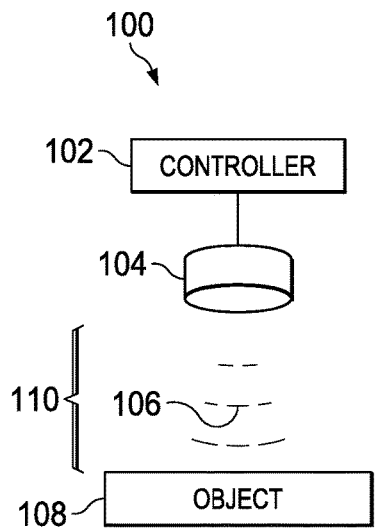
FIGS. 1A-1B are diagrams illustrating an example environment including an example controller in communication with an example ultrasonic transducer to obtain distance measurements of an object.

Oscillating objects display particular characteristics that can be measured and analyzed. In order to measure and analyze the vibrations of objects, previous methods have involved either installing a meter on the object to be measured or detecting ultrasonic sound waves emitted from the object that are otherwise unheard (e.g., due to ultrasonic waves being outside the audible domain).

On-object meters are often implemented using accelerometers, which detect gravitational forces (e.g., redistribution of weight, shock, falling, etc.). These on-object meters must be mounted on the device to be measured, because the accelerometer detects gravitational forces as applied to the accelerometer (e.g., if the object moves, the accelerometer will only move, and thus report such movement, if it is attached to the object). Because such meters need to be mounted on objects to measure the same, the meters are subject to substantial wear, varying temperatures, contaminants, moving parts, and other volatile environments. Accordingly, such devices require frequent replacement, repair, and/or configuration.

Additionally, it is often difficult to report the measurements acquired by on-object meters, especially meters that are positioned on moving parts (e.g., a motor). Thus, the on-device meter has to wirelessly transmit data, be wired in such a way to avoid severing the wired connection, and/or be removed for such reporting purposes. Any wireless devices and/or complex wiring is also subject to the substantial wear, varying temperatures, contaminants, moving parts, and other volatile environments as the meters themselves.

The detection of ultrasonic sound waves emitted from objects often involves a probe attached to an audio producing device (e.g., headphones, speakers, etc.) to convert inaudible sound waves into audible sound. However, often the only way to receive a precise reading requires the probe to be in direct contact with the object and in the same orientation as the emitted ultrasonic waves. Further, ultrasonic sound waves emitted from the object merely provide an association between a particular audible sound with a particular operation. Such probing devices do not provide a high level of detail regarding the characteristics of a vibrating object (e.g., the converted ultrasonic sound waves do not establish a vibration frequency, displacement, phase, etc.).

Additionally, ultrasonic waves are subject to noise (e.g., interference) from other related or unrelated sound waves. Therefore, the sound converted by the probe and audio producing devices is often not even a true representation of only the ultrasonic sound waves emitted from the object. The comparison of the level of a desired signal to the level of background noise is called the signal to noise ratio ("SNR") and is often expressed in decibels (e.g., dB). A high SNR (e.g., greater than 0 dB) indicates more signal than noise, while a low SNR (e.g., less than 0 dB) indicates more noise than signal. To obtain a higher SNR, filters are used to remove noise or other unwanted signals. Noise can affect the amplitude, frequency, and/or phase of a signal and specific filters are required to correct each type of unwanted artifact. When probing for sound waves emitted from objects, it is often difficult to distinguish noise from signal, and therefore, difficult to determine what filtering arrangement to use.

The example methods and apparatus of the present disclosure, in contrast, provide off-device measurement using ultrasonic transducers (e.g., transmitters, receivers, transceivers, etc.) to measure variances in the distance between the ultrasonic transducers and the object to be measured to determine vibration characteristics of the object. The example methods and apparatus generate ultrasonic waves with particular known characteristics (e.g., frequency) to measure variances in distance of an oscillating object, which provide higher levels of detail than the conversion of ultrasonic sound waves emitted from objects into the audible and/or visual domains.

Figure 1B:
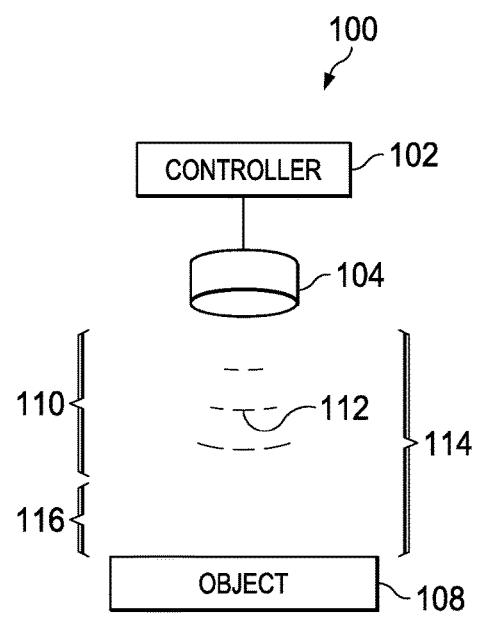

FIGS. 1A-1B are diagrams illustrating an example environment 100 including an example controller 102 in communication with an example ultrasonic transducer 104. In the illustrated example, the example ultrasonic transducer 104 is a transceiver that is capable of sending and receiving ultrasonic waves. The example ultrasonic transducer 104 converts electrical signals (e.g., voltage, current, etc.) to ultrasonic waves when electrical signals are applied to a piezoelectric sensor within the example ultrasonic transducer 104. The electrical signals causes the piezoelectric sensor to oscillate and emit ultrasonic waves. This process is reversed when the example ultrasonic transducer 104 receives ultrasonic waves. The received ultrasonic waves cause the piezoelectric sensor to oscillate and generate electrical signals. In some examples, transmission and reception of ultrasonic waves (e.g., sampling) may interfere with each other (e.g., oscillation due to transmission is still occurring when ultrasonic waves are received, oscillation due to reception is still occurring when ultrasonic waves are transmitted, etc.) The example methods and apparatus disclosed herein compensate for such interferences by transmitting phase shifted ultrasonic waves at lower frequencies when the ultrasonic transducer 104 is oscillating from a previous transmission and/or reception of ultrasonic waves. In the illustrated example, the example ultrasonic transducer 104 creates ultrasonic waves with a frequency of 400 kilohertz ("kHz"). Additionally and/or alternatively, ultrasonic waves having different frequencies may be used (e.g., 40 kHz, 100 kHz, etc.).

In FIG. 1A, the example ultrasonic transducer 104 sends example ultrasonic waves 106 towards an example object 108 to obtain a first distance measurement of the example object 108. The example ultrasonic waves 106 travel from the example ultrasonic transducer 104 through a medium, such as, for example, the air, towards the example object 108. Additionally or alternatively, the example ultrasonic transducer 104 may send ultrasonic waves through other mediums, such as liquids. The example ultrasonic waves 106 reflect off the example object 108 and travel back towards the example ultrasonic transducer 104. The example controller 102 controls when the example ultrasonic transducer 104 sends the example ultrasonic waves 106, recognizes when the example ultrasonic transducer 104 receives an echo of the example ultrasonic waves 106 (e.g., the example ultrasonic waves 106 returning from reflecting off an object, such as the example object 108), and determines the time between the sending and the receiving of the ultrasonic waves 106 (e.g., time of flight). The example controller 102 determines the distance between the example transducer 104 and the example object 108 based on the time of flight of the example ultrasonic waves 106 and the speed of sound (e.g., 343 meters per second (m/s)). In the illustrated example of FIG. 1A, the example controller 102 determines that the example object 108 is a first distance 110 away from the example ultrasonic transducer 104.

In FIG. 1B, the example ultrasonic transducer 104 sends example ultrasonic waves 112 towards the example object 108 to obtain a second distance measurement of the example object 108. In the illustrated example, the example controller 102 determines that the example object 108 is a second distance 114 away from the example ultrasonic transducer 104. The example controller 102 further determines that the second distance 114 is greater than the first distance 110 by a third distance 116. In some examples, when the example controller 102 determines the example object 108 oscillates between the first distance 110 and the second distance 114, the example controller 102 determines that the example object 108 is vibrating. The example controller 102 further determines vibration characteristics (e.g., frequency, amplitude, phase, etc.) of the example object 108, as further discussed herein. For example, the example controller 102 determines that the example third distance 116 is the total displacement of the example object 108. The example controller 102 then determines that half the example third distance 116 (e.g., half the total displacement) is the amplitude of the example object 108 from rest. Alternatively, the first distance 110 may represent the example object 108 at rest and the example second distance 114 may represent the maximum distance the example object 108 is from the example ultrasonic transducer 104. In such examples, the difference between the example second distance 114 and the example first distance 110 (e.g., the example third distance 116) is the actual amplitude of the example object 108.

While the examples of FIGS. 1A-1B illustrate one ultrasonic transducer, other numbers of ultrasonic transducers, ultrasonic transmitters, and/or ultrasonic receivers may be used in replace of or in conjunction with the example ultrasonic transducer 104. In some examples, multiple ultrasonic transducers are used to measure multiple surfaces of the example object 108 (e.g., a first ultrasonic transducer measures a first surface and a second ultrasonic transducer measures a second surface).

Figure 2:
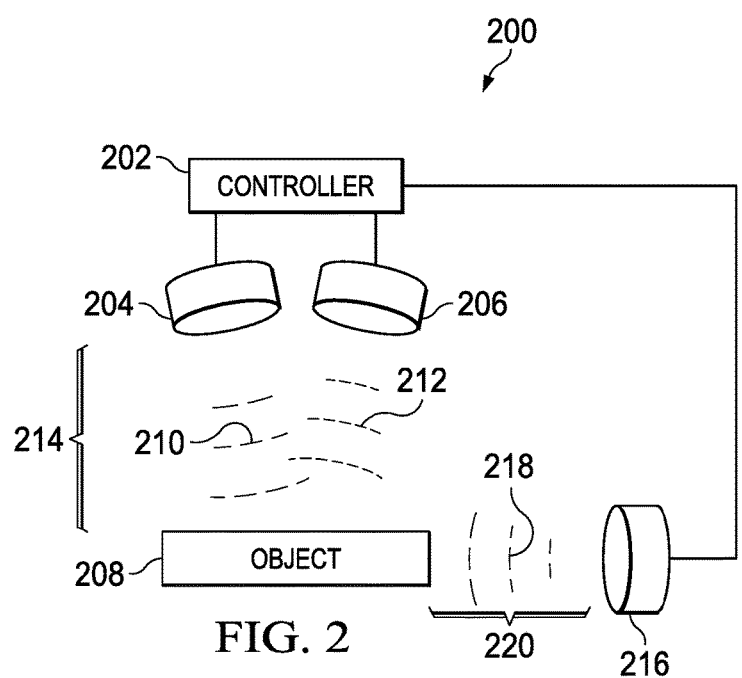
FIG. 2 is a diagram illustrating an example environment including an example controller in communication with an example ultrasonic transmitter and an example ultrasonic receiver to obtain distance measurements of an object.

FIG. 2 is a diagram illustrating an example environment 200 including an example controller 202 in communication with an example ultrasonic transmitter 204 and an example ultrasonic receiver 206 to obtain distance measurements of an object 208. In some examples, the example controller 202 is similar to the example controller 102 in FIGS. 1A-1B. In the illustrated example, the example ultrasonic transmitter 204 sends example ultrasonic waves 210 towards the example object 208 in a first direction. The example ultrasonic waves 210 reflect off the example object 208 and form example reflected waves 212. The example ultrasonic receiver 206 receives the example reflected waves 212. The example controller 202 determines the time between the transmission of the example ultrasonic waves 210 and the receipt of the example reflected waves 212 to obtain a first distance measurement 214 of the example object 208. Additionally or alternatively, the example ultrasonic transmitter 204 and/or the example ultrasonic receiver 206 may be ultrasonic transceivers that both transmit and receive ultrasonic waves.

In the illustrated example, an ultrasonic transducer 216 in communication with the example controller 202 sends example ultrasonic waves 218 towards the example object 208 in a second direction. The example ultrasonic waves 218 reflect off the example object 208 and return to the example ultrasonic transducer 216. The example controller 202 determines the time between the transmission and receipt of the example ultrasonic waves 218 to obtain a second distance measurement 220 of the example object 208. Thus, in the illustrated example, the example controller 202 determines variations in distance (e.g., vibration) in the first and second directions.

Accordingly, the example methods and apparatus disclosed herein determine vibration characteristics of the example object 108, 208 while being disposed a distance away from the example object 108, 208. Thus the example controller 102, 202 and the example ultrasonic transducer 104, the example ultrasonic transmitter 204, the example ultrasonic receiver 206, and/or the example ultrasonic transducer 216 are not subject to the same substantial wear, contaminants, moving parts, and other volatile environments to which on-device meters are subjected. Additionally, the example methods and apparatus save power by uniformly sampling with low power ultrasonic transmitters, receivers, and/or transducers.

Figure 3:
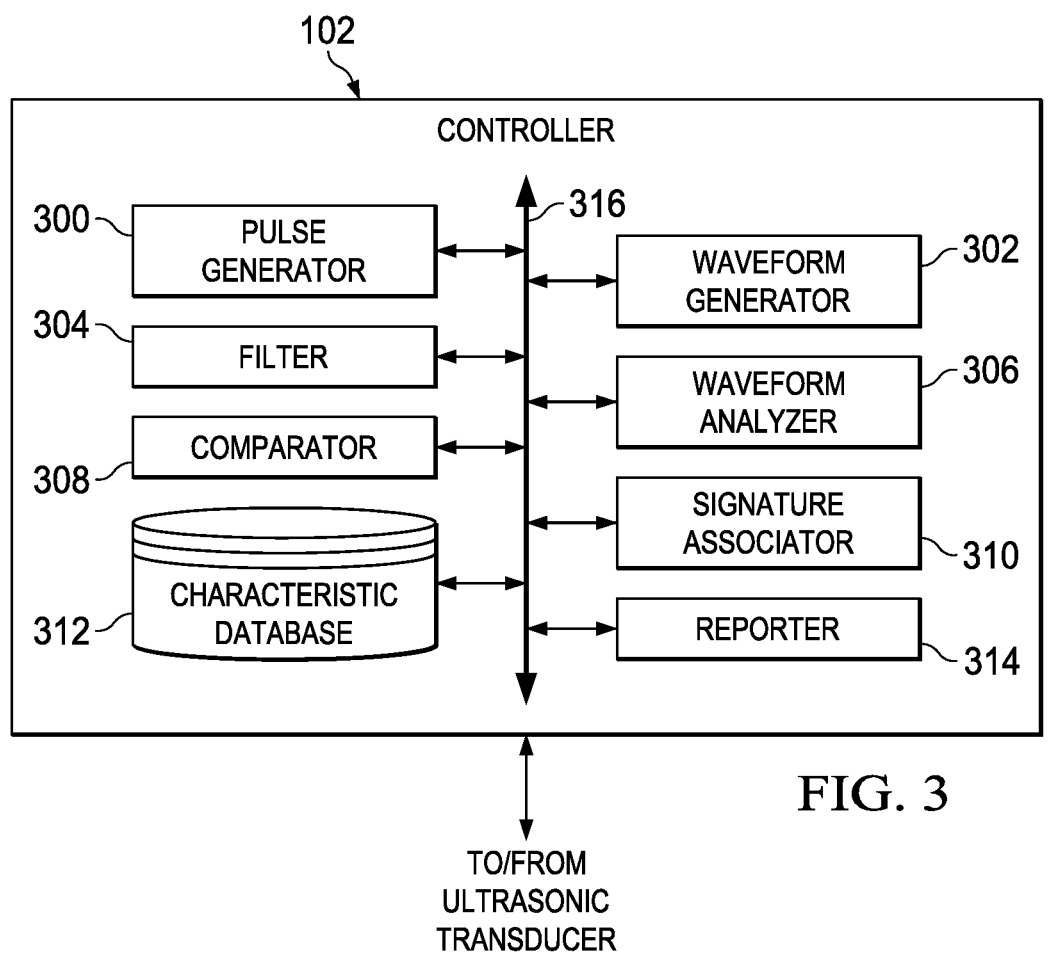
FIG. 3 is a block diagram illustrating the example controller of FIGS. 1A-1B.

FIG. 3 is a block diagram illustrating the example controller 102 of FIGS. 1A-1B. In some examples, the example controller 102 embodies or is in communication with one or more additional components including, for example, a low noise amplifier ("LNA"), an analog front end ("AFE"), an analog to digital converter ("ADC"), a power supply, a bandpass filter circuit, a time to digital converter ("TDC"), a Hilbert transform finite impulse response ("FIR") filter, or other like components. In some examples, ultrasonic wave characteristics are affected by temperature, local atmospheric variations, air conditioning, humidity, air density, etc. The example methods and apparatus compensate for such variances. In such examples, the example controller 102 embodies or in communication with a temperature sensor to provide start and stop signals proportional to the temperature sensed. Additionally or alternatively, the example pulse generator 300 may adapt the sampling frequency of the example ultrasonic transducer 104 in response to variations in the environment.

The example controller 102 includes an example pulse generator 300, an example waveform generator 302, an example filter 304, an example waveform analyzer 306, an example comparator 308, an example signature associator 310, an example characteristic database 312, and an example reporter 314, all in communication via an example bus 316. The example bus 316 enables communication between the example controller 102 and the example ultrasonic transducer 104.

The example pulse generator 300 triggers the sending of ultrasonic waves (e.g., example ultrasonic waves 106, 112) from the example ultrasonic transducer 104. For example, the example pulse generator 300 triggers a burst of pulses (e.g., three) that instruct the example ultrasonic transducer to send the same number of ultrasonic waves (e.g., three) towards the example object 108. The example pulse generator 300 can trigger any number of pulses within a burst as necessary to obtain accurate readings of the example object 108. Additionally, the example pulse generator 300 controls the frequency at which each burst of pulses is sent (e.g., the sampling frequency fs). In the illustrated example, the example pulse generator 300 samples at a frequency fs of 120 Hz. Additionally or alternatively, the example pulse generator 300 may sample at alternate frequencies (e.g., 60 Hz, 240 Hz, etc.). To detect the frequency at which an object is vibrating, the example pulse generator 300 samples at a frequency at least twice as fast as the example object 108 is suspected to be vibrating (e.g., sampling frequency of 120 Hz for an object vibrating at 60 Hz). In some examples, the example pulse generator 300 adapts the sampling frequency fs due to temperature variations, transmission and reception interference, or other conditions.

The example waveform generator 302 creates or otherwise generates a waveform based on a plurality of sample points (e.g., sample data) acquired by the example ultrasonic transducer 104 (FIGS. 1A-1B). For example, each pulse sent by the example ultrasonic transducer 104 returns information regarding the distance of the example object 108 at a particular point in time (e.g., a sample point). The example waveform generator 302 utilizes a plurality of distance data at different sample points (e.g., points in time) to generate a waveform representing the vibration of the example object 108. According to Fourier series, the example waveform generator 302 can define the waveform as a summation of sine and/or cosine waves, which simplifies analysis of the waveform. In some examples, storing all data corresponding to each sample point may lead to memory overflow, overwriting data, loss of data, or other consequences. Therefore, the example waveform generator 302 generates the waveform based on successive uniform sampling of the data acquired by the example ultrasonic transducer 104.

Example waveforms that the example waveform generator 302 creates include waveforms in the sample domain (e.g., distance (y-axis) measured by each pulse (x-axis)), the frequency domain (e.g., normalized amplitude (y-axis) by frequency (x-axis) (e.g., fast Fourier transform of the sample domain)), phase domain (e.g., phase (y-axis) by time (x-axis)), or the time domain (e.g., distance (y-axis) by time (x-axis), velocity (y-axis) by time (x-axis), acceleration (y-axis) by time (x-axis), etc.). Initially, the example waveform generator 302 creates a vibration displacement waveform in the sample domain (e.g., distance (x-axis) by each pulse (x-axis)).

The highest frequency waveform that the example waveform generator 302 can create is based the Nyquist frequency. The Nyquist frequency is half of the sampling frequency fs in a discrete signal processing system. To reconstruct an original waveform with a frequency f, the Nyquist frequency (e.g., fs/2) has to be greater than the absolute value of the waveform frequency f (e.g., fs/2>|f|). Otherwise, an alias waveform will be created instead of the original waveform. Aliasing is to be avoided, as incorrect vibration characteristics may be recorded if an alias waveform is constructed instead of the original waveform.

The example filter 304 receives the created waveform from the example waveform generator 302. In the illustrated example, the example filter 304 applies one or more filters to the created waveform to resolve ultrasonic signals from noise. In some examples, the example filter 304 applies a bandpass filter to the generated waveform to keep certain frequencies (e.g., within a passband) and exclude other frequencies. An example bandpass filter is a resistor-inductor-capacitor (RLC) circuit. Alternatively, combining a high pass filter (e.g., a capacitor connected to a load and a resister in parallel) to exclude low frequencies and a low pass filter (e.g., a resister connected to a load and capacitor in parallel) to exclude high frequencies achieves the same result of a bandpass filter. For example, a bandpass filter centered at 400 kHz applied to the created waveform would keep data related to the example ultrasonic transducer 104, which operates at 400 kHz, while removing other frequencies, such as 4 kHz, which may be background noise that would otherwise disrupt data from the example ultrasonic transducer 104.

In some examples, the example filter 304 applies a Hilbert transform FIR filter to the generated waveform to shift the phase of the generated waveform. For example, by taking advantage of the corollary that $\sin(-\omega t+\theta)$ is indistinguishable from $\sin(\omega t-\theta+\pi)$ and $\cos(-\omega t+\theta)$ is indistinguishable from $\cos(\omega t-\theta)$ and applying the Hilbert transform FIR filter, the example filter 304 can represent the generated waveform in just positive frequencies (e.g., $\omega$). In the illustrated example, the example filter 304 distinguishes the original waveform from aliases by applying both a bandpass filter and a Hilbert transform FIR filter to modulate the amplitude and phase of the signal received by the example ultrasonic transducer 104. In the illustrated example, the example filter 304 outputs the resolved waveform to the example waveform analyzer 306.

The example waveform analyzer 306 determines characteristics of the example object 108 from the resolved waveform from the example filter 304. Example characteristics of the resolved waveform include Height (e.g., displacement of the example object 108), Amplitude (e.g., displacement of the example object 108 from rest), Frequency (e.g., cycles per second), Velocity (e.g., distance per second), or Acceleration (e.g., distance per second squared).

In the illustrated example, the example waveform analyzer 306 applies a high resolution algorithm to the filtered displacement waveform (e.g., amplitude by sample) to obtain subwavelength resolution (e.g., resolution at a dimension smaller than the wavelength). The example filter 304 envelopes the generated waveform, performs phase linear regression on a plurality of points around a first time, and determines subwavelength resolution based on the zero crossing nearest the first time. To envelope the generated waveform, the example waveform analyzer 306 inputs the bandpass filtered waveform through an envelope detector circuit (e.g., a diode connected to a capacitor, a resistor, and a load in parallel). The envelope effectively outlines at least one of an upper or lower bound of the waveform to generalize the amplitude of the waveform. As discussed herein, the example methods and apparatus utilize an upper bounded envelope, however, the example disclosed methods and apparatus may alternatively use a lower bounded envelope without departing from the scope of the present disclosure.

The waveform analyzer 306 determines a first time wherein the enveloped amplitude is greater than half of the maximum enveloped amplitude. The waveform analyzer 306 further identifies a plurality of sample points (e.g., 10) of the waveform that surround the first time. The waveform analyzer 306 performs linear regression on the plurality of sample points (e.g., determining the best fitting line amongst the plurality of sample points) in the phase domain (e.g., phase by time) and identifies a zero crossing nearest to the first time. From the nearest zero crossing, the example waveform analyzer 306 identifies the portion of the waveform to analyze for accurate distance measurement of the example object 108. In the illustrated example, the example waveform analyzer 306 identifies displacement of the example object 108 with 100 micrometer (e.g., μm) precision. For example, the example third distance 204 (FIG. 2) may only be 100 μm, which would otherwise be undetected without the high resolution algorithm disclosed herein. While the aforementioned example discusses displacement, or amplitude (e.g., distance), other characteristics of the example object 108 (e.g., frequency, wavelength, height, phase, velocity, acceleration, etc.) can be similarly determined. In the illustrated example, the example waveform analyzer 306 outputs the determined characteristic(s) (e.g., distance, frequency, wavelength, height, phase, velocity, acceleration, etc.) to the example comparator 308.

The example comparator 308 receives the output of the example waveform analyzer 306 and accesses the example characteristic database 312. The example comparator 308 searches example characteristic database 312 for characteristic(s) matching (e.g., substantially similar) to the determined characteristic(s) from the example waveform analyzer 306. For example, the example waveform analyzer 306 may have identified the example object 108 has a displacement of 10 millimeters at a frequency of 40 hertz. If such characteristics have previously been measured by the example methods and apparatus disclosed herein, or otherwise stored in the example characteristic database 312, the example comparator 308 identifies such characteristics in the characteristic database 312. Such characteristics may additionally be associated with an identifier (e.g., an identity of the object, a status of the object, etc.). The example comparator 308 outputs the determined characteristics and/or any associated identifier to the example reporter 314. In some examples, the example comparator 308 outputs the determined characteristics to the example signature associator 310.

The example signature associator 310 receives determined characteristics from the example comparator 308. In the illustrated example, the example signature associator 310 receives such characteristics when the example comparator 308 does not identify matching characteristics in the example characteristic database 312. The example signature associator 310 identifies the determined characteristics as a signature of the example object 108. The example signature associator 310 additionally associates the signature with an identity of the example object 108 (e.g., what kind of object is the example object 108), a status of the example object 108 (e.g., normal, abnormal, on, off, etc.), or other known identifier (e.g., vibration pattern associated with a person's voice reverberating off the example object 108, vibration pattern associated with a person's walking pattern on the example object 108, etc.). In some examples, the example signature associator 310 associates a simple identifier, such as "known" (e.g., identifying that this particular characteristic or set of characteristics has previously been identified). In such examples, the example reporter 314 can identify when "unknown" (e.g., not previously identified) characteristics are identified, as further discussed below. In the illustrated example, the example signature associator 310 associates complex identifiers, such as specific data about the example object 108. The specific data may be manually identified by an operator of the example methods and apparatus disclosed herein, loaded from a definition library of characteristics of known objects, or other know method of data entry. Additionally or alternatively, the specific data may be identified by searching a network (e.g., the Internet) for substantially similar characteristics. The example signature associator 310 outputs the determined characteristics and any associated identifiers to at least one of the example characteristic database 312 or the example reporter 314.

The example characteristic database 312 stores characteristics associated with signatures created by the example signature associator 310 and/or characteristics associated with signatures retrieve from third party sources (e.g., the Internet, operator data entry, definition library, etc.). In the illustrated example, the example characteristic database 312 is a storage device (e.g., a hard drive, solid state drive, floppy disk, compact disk, Blu-ray disk, RAID system, digital versatile disk (DVD), etc.) disposed within the example controller 102. Alternatively, the example characteristic database 312 may be hosted and/or controlled by a third party (e.g., an external storage device connectable through a network).

The example reporter 314 receives determined characteristics and/or identifiers from at least one of the example comparator 308 or the example signature associator 310. Based on the type of identifier, the example reporter 314 reports an alert, a status, a description, or other information associated with the determined characteristics and identifiers.

For example, when first characteristics are associated with a first identifier indicating the example object 108 is operating normally, the example reporter 314 reports a normal status for the example object 108. When second characteristics are associated with a second identifier indicating the example object 108 is not operating normally, the example reporter 314 reports an abnormal status for the example object 108. Therefore, in such examples, the example methods and apparatus are a fault detector, wherein the example reporter 314 reports possible faults, often before such faults become a much larger problem.

When third characteristics are associated with a third identifier indicating the example object 108 is not moving, the example reporter 314 reports that the example object 108 is powered off. Therefore, in such examples, the example reporter 314 reports on/off frequency, power issues, power consumption, duty cycle, or other related power concerns.

When fourth characteristics are associated with a fourth identifier indicating known characteristics have been measured in association with the example object 108, the example reporter 314 describes the known characteristics. Therefore, in such examples, the example methods and apparatus are an identity detector, wherein the example reporter 314 identifies and reports patterns associated with known objects, voices, walking patterns, and other vibration causing biometrics that are frequently measured the example methods and apparatus disclosed herein. When fifth characteristics are associated with a fifth identifier indicating unknown characteristics have been measured in association with the example object 108, the example reporter 314 generates an alert. Therefore, in such examples, the example methods and apparatus are a security system, wherein the example reporter 314 generates an alert when unknown voices, walking patterns, etc. are identified.

Figure 4:
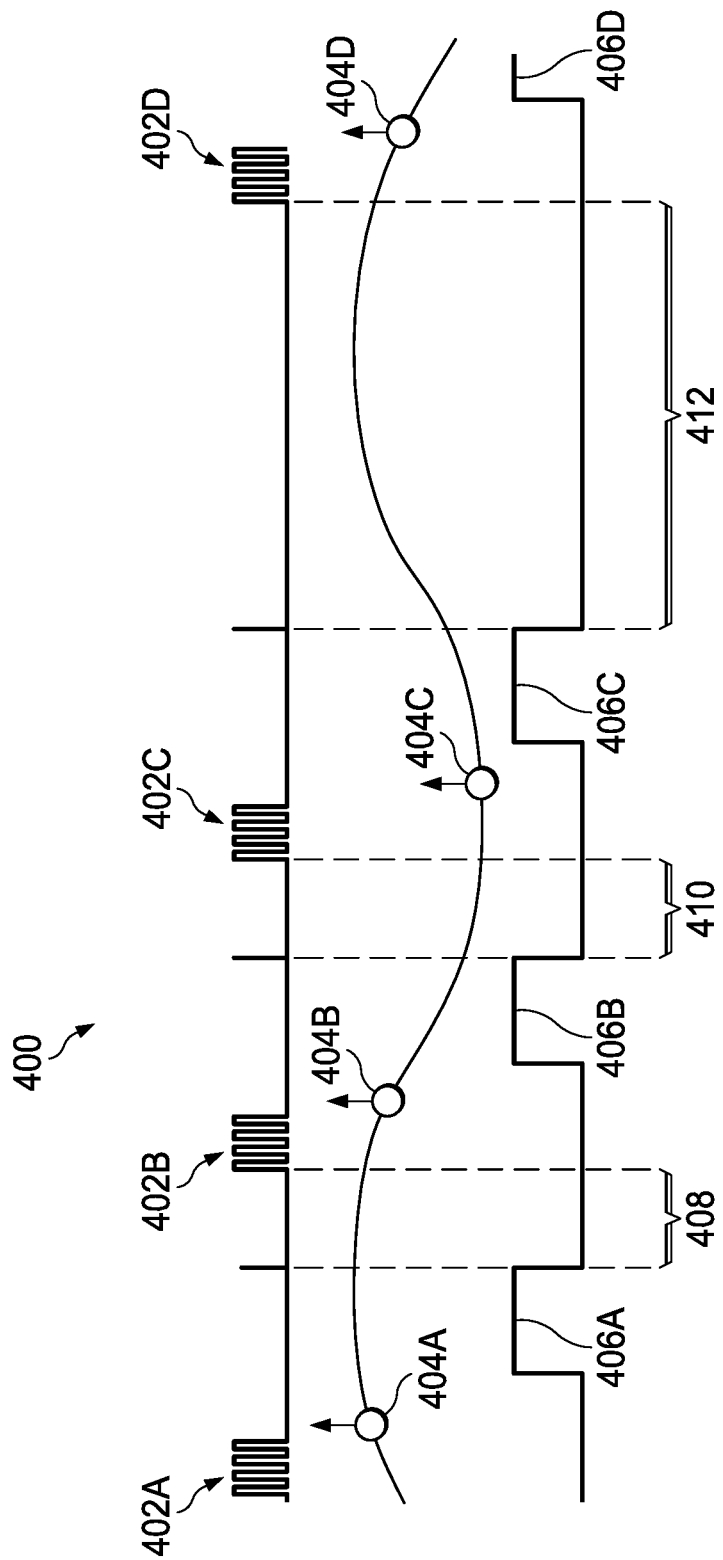
FIG. 4 is a diagram illustrating example interactions between the example transducer and example object of FIGS. 1A-1B.

FIG. 4 is a diagram illustrating an example operation 400 between the example controller 102, the example transducer 104, and the example object 108 of FIGS. 1-3. In operation, the example pulse generator 300 (FIG. 3) generates one or more example bursts 402a, 402b, 402c, 402d of pulses prompting the example ultrasonic transducer 104 (FIGS. 1A-1B) to send ultrasonic waves towards the example object 108 (FIGS. 1A-1B). As illustrated in FIG. 4, the example object 108 has an oscillation defined by at least example points 404a, 404b, 404c, 404d. The ultrasonic waves produced by the example ultrasonic transducer 104 traverse a medium (e.g., the air) and are reflected off of the example object 108 at example points 404a, 404b, 404c, 404d (e.g., example burst 402a reflects off of the example object 108 at example point 404a, example burst 402b reflects off of the example object 108 at example point 404b, example burst 402c reflects off of the example object 108 at example point 404c, example burst 402d reflects off of the example object 108 at example point 404d). The example pulse generator 300 identifies receipt of reflected ultrasonic waves (e.g., example bursts 402a, 402b, 402c, 402d returning to the example ultrasonic transducer 104) by the example ultrasonic transducer 104 at example locations 406a, 406b, 406c, 406d. In the illustrated example, the reflected example bursts 402a, 402b, 402c, 402d are converted from an analog signal to a digital signal (e.g., a constant "1" or high).

In the illustrated example, upon receipt of the example reflected ultrasonic waves (e.g., at example locations 406a, 406b), the example waveform generator 302 determines the time of flight (e.g., the time between sending an ultrasonic wave(s) toward an object and receiving a reflected ultrasonic wave(s)) of the example bursts 402a, 402b. Subsequently, during periods 408, 410, the example waveform generator 302 stores the time of flight for example bursts 402a, 402b, prior to the example pulse generator transmitting example burst 402c. Although the illustrated example is described with reference to determining and storing the time of flight for example bursts 402a and 402b, the process of sending pulses, receiving reflections, determining and storing the time of flight may repeat for many iterations until enough sample points are captured and stored to reconstruct a complete waveform of the example object 108.

In some examples, the example ultrasonic transducer 104 is still oscillating due to receipt of reflected example burst 402a when the example pulse generator 300 transmits example burst 402b (e.g., the ultrasonic transducer 104 reverberates due to receipt of example burst 402a and is instructed to transmit example burst 402b prior to the reverberations ceasing). For example, if the example object 108 is vibrating at 100 Hz, a sampling rate of 200 Hz may not provide enough time for the example ultrasonic transducer 104 to recover from example burst 402a (e.g., stop oscillating from transmission and/or receipt of previous ultrasonic waves) before transmission of example burst 402b. In such examples, the continuing reverberations may interfere with example burst 402b. Accordingly, the example pulse generator 300 identifies whether the example ultrasonic transducer 104 is reverberating prior to transmitting example burst 402b. In the illustrated example, the example pulse generator 300 transmits a series of pulses that are phase shifted at lower frequencies (e.g., lower than the frequencies sent during example burst 402a) during the example burst 402b. When the example ultrasonic transducer 104 receives example burst 402b (e.g., the phase shifted lower frequency series of pulses), the example filter 304 distinguishes example burst 402b from oscillation due to example burst 402a. The example waveform generator 302 therefore obtains accurate data from both example burst 402a and example burst 402b, even where interference between bursts would normally occur.

In the illustrated example, the example waveform generator 302 stores data from period 408 after the example pulse generator 300 identifies receipt of reflected ultrasonic waves by the example ultrasonic transducer 104 at example location 406a and prior to the example pulse generator 300 transmitting example burst 402b. In some examples, the transmission of subsequent bursts (e.g., 402b) is delayed until data from period 408 is stored. In some examples, the example pulse generator 300 generates bursts at a fixed rate independent of whether data has been stored by the example waveform generator 302. In such examples, the example pulse generator 300 transmits a series of pulses that are phase shifted at lower frequencies during the subsequent burst (e.g., 402b). The sampling time varies depending on the vibration frequency of the example object 108. For example, when the example object 108 is vibrating at a very low frequency, the example methods and apparatus sample for a long time period, and when the example object 108 is vibrating at a high frequency, the example methods and apparatus sample for a shorter time period. As noted above, the sampling frequency and phase may adapt as well.

After the example waveform generator 302 stores time of flight data during periods 408, 410, the example waveform generator 302 generators an example waveform during period 412 based on the data stored in periods 408, 410. As illustrated in FIG. 4, only two periods 408, 410 are depicted wherein the example waveform generator 302 stores data.

However, any number of periods may be used to obtain additional sample points and achieve better resolution of the oscillations of the example object 108.

After the example waveform generator 302 generates the example waveform, the example filter 304 applies one or more filters to the generated waveform to resolve ultrasonic signals from noise. Thereafter, the example waveform analyzer 306 determines characteristics of the example object 108 from the resolved waveform from the example filter 304. The example comparator 308 receives the output of the example waveform analyzer 306 and accesses the example characteristic database 312 to identify any known signatures associated with the characteristics determined by the example waveform analyzer 306.

When no known signatures associated with the characteristics determined by the example waveform analyzer 306 are located by the example comparator 308, the example signature associator 310 identifies the determined characteristics as a signature of the example object 108 and associates the signature with an identity of the example object 108, a status of the example object 108, or other known identifier. The example characteristic database 312 stores characteristics associated with signatures created by the example signature associator 310.

The example reporter 314 reports an alert, a status, a description, or other information associated with the determined characteristics and identifiers. When one or more known signatures associated with the characteristics determined by the example waveform analyzer 306 are located by the example comparator 308, the example reporter 314 reports a status, description, or identity associated with the signature. When no known signatures are located by the example comparator 308, the example reporter 314 reports an alert, indicating unknown characteristics have been identified.

In some examples, the example comparator 308 identifies characteristics in the example characteristic database 312 matching characteristics only partially measured by the example ultrasonic transducer 102 (e.g., characteristics are matched prior to completion of a long sample period). In such examples, the aforementioned process may be streamlined to increase efficiency and decrease processing. Additionally, frequently measured characteristics may be subject to the same streamline processing. The streamline processing may be implemented by storing more frequently detected characteristics in more easily accessible memory (e.g., cache memory), processing smaller wave functions (e.g., portions of the generated waveform), or other streamline processes apparent to one of ordinary skill in the art.

While an example manner of implementing the example controller of FIGS. 1A-1B is illustrated in FIG. 3, one or more of the elements, processes and/or devices illustrated in FIG. 3 may be combined, divided, re-arranged, omitted, eliminated and/or implemented in any other way. Further, the example pulse generator 300, the example waveform generator 302, the example filter 304, the example waveform analyzer 306, the example comparator 308, the example signature associator 310, the example characteristic database 312, the example reporter 314, the example bus 316, and/or, more generally, the example controller 102 of FIG. 3 may be implemented by hardware, software, firmware and/or any combination of hardware, software and/or firmware. Thus, for example, any of the example pulse generator 300, the example waveform generator 302, the example filter 304, the example waveform analyzer 306, the example comparator 308, the example signature associator 310, the example characteristic database 312, the example reporter 314, the example bus 316, and/or, more generally, the example controller 102 of FIG. 3 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example pulse generator 300, the example waveform generator 302, the example filter 304, the example waveform analyzer 306, the example comparator 308, the example signature associator 310, the example characteristic database 312, the example reporter 314, the example bus 316, and/or, more generally, the example controller 102 of FIG. 3 is/are hereby expressly defined to include a tangible computer readable storage device or storage disk such as a memory, a digital versatile disk (DVD), a compact disk (CD), a Blu-ray disk, etc. storing the software and/or firmware. Further still, the example controller 102 of FIGS. 1-3 may include one or more elements, processes and/or devices in addition to, or instead of, those illustrated in FIG. 3, and/or may include more than one of any or all of the illustrated elements, processes and devices.

Figure 5:
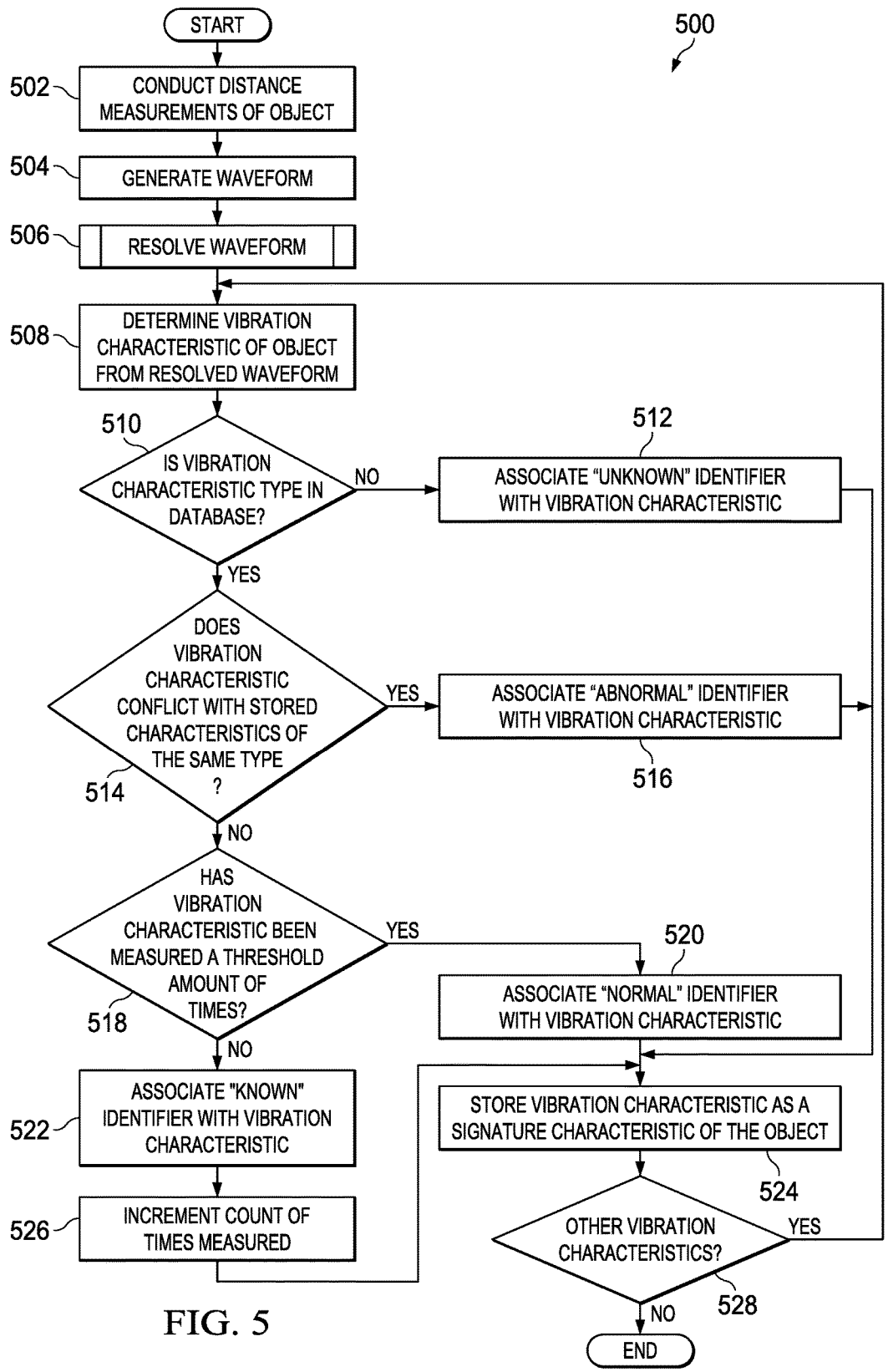
FIGS. 5-6 are flow charts illustrating example instructions to implement the example controller of FIGS. 1A-1B and 3.
Figure 6:
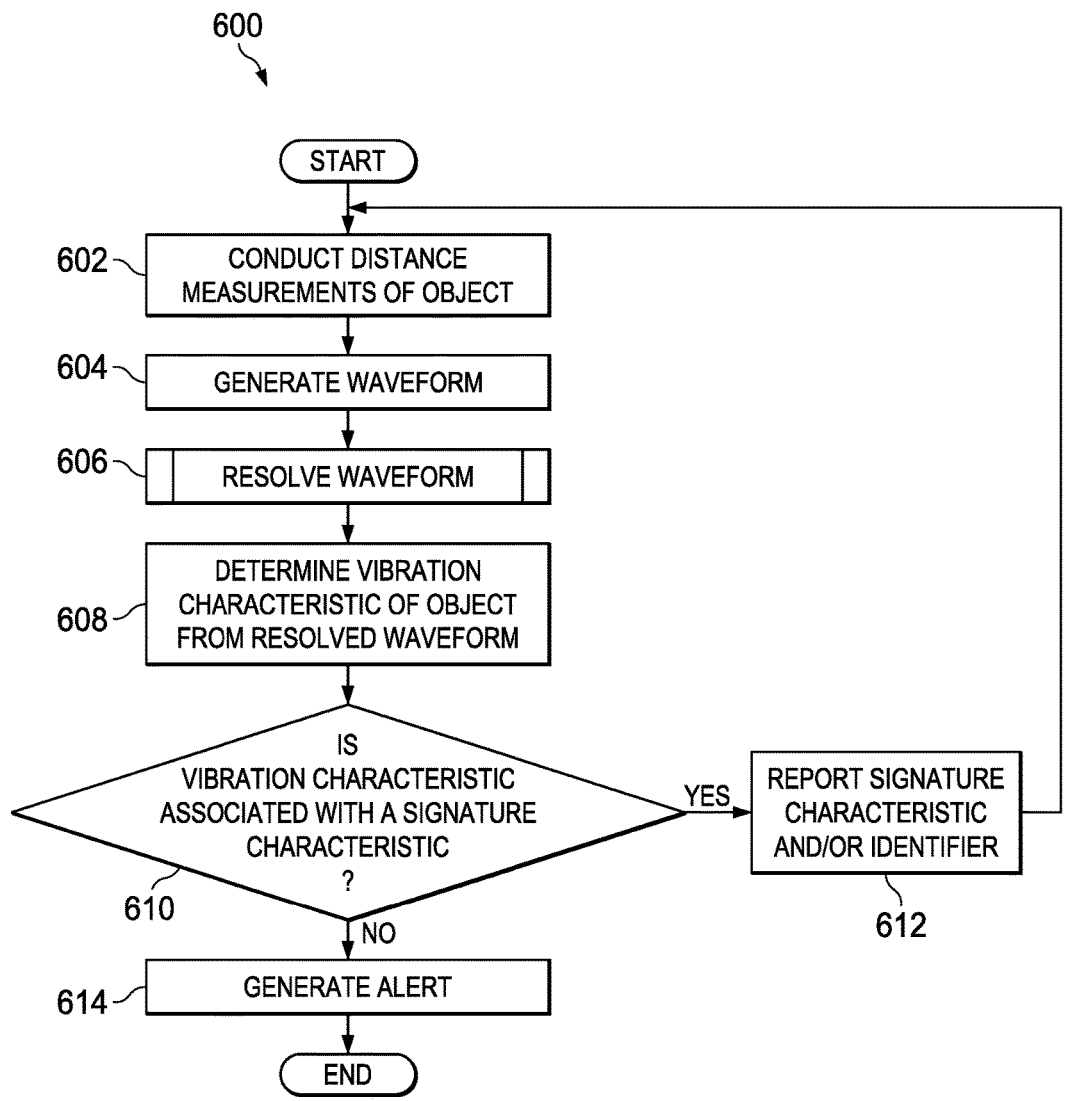
Figure 7:
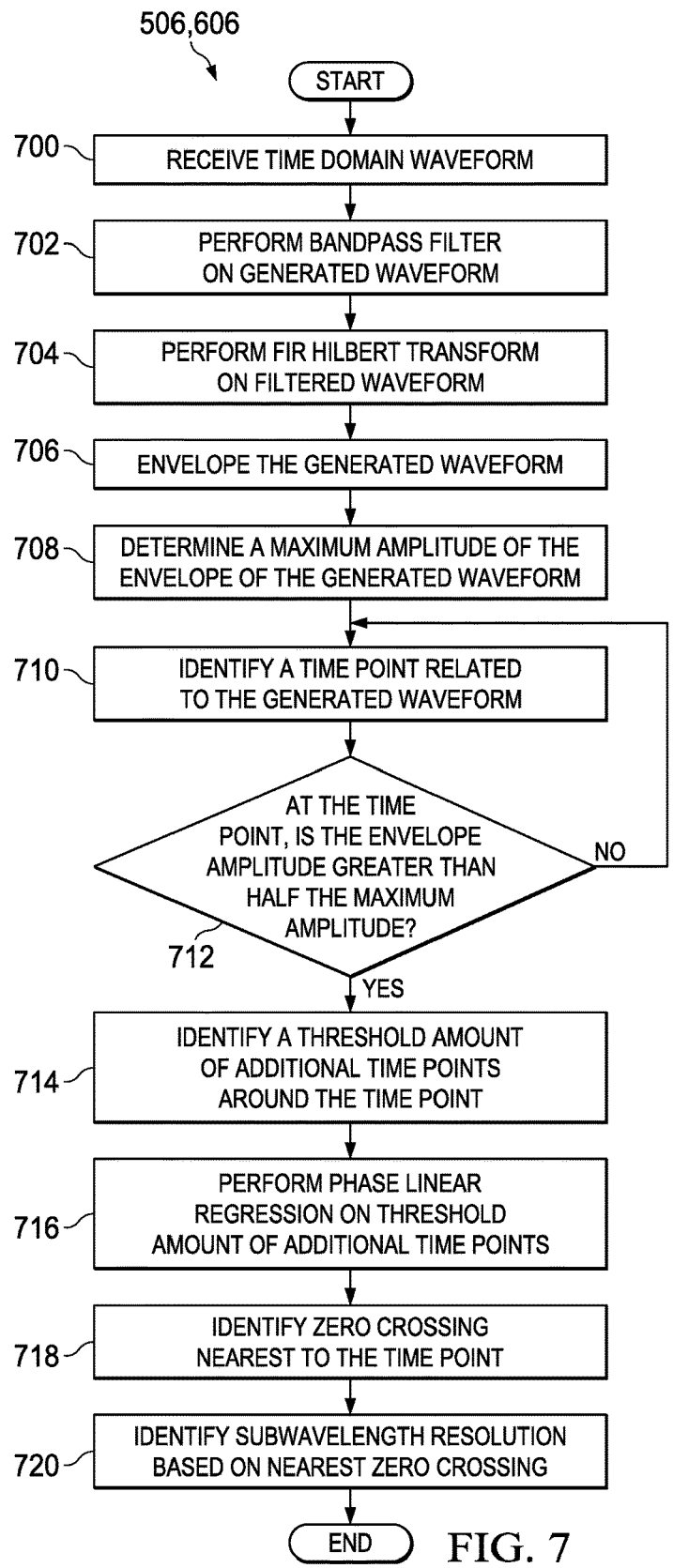
FIG. 7 is a flow chart illustrating example instructions to implement an example filter and an example waveform analyzer of FIG. 3.

Flowcharts representative of example machine readable instructions for implementing the example controller 102 of FIG. 3 is shown in FIGS. 5-7. In this example, the machine readable instructions comprise a program for execution by a processor such as the processor 8 shown in the example processor platform 800 discussed below in connection with FIG. 8. The program may be embodied in software stored on a tangible computer readable storage medium such as a CD-ROM, a floppy disk, a hard drive, a digital versatile disk (DVD), a Blu-ray disk, or a memory associated with the processor 812, but the entire program and/or parts thereof could alternatively be executed by a device other than the processor 812 and/or embodied in firmware or dedicated hardware. Further, although the example program is described with reference to the flowchart illustrated in FIGS. 5-7, many other methods of implementing the example controller 102 may alternatively be used. For example, the order of execution of the blocks may be changed, and/or some of the blocks described may be changed, eliminated, or combined.

As mentioned above, the example processes of FIGS. 5-7 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and transmission media. As used herein, "tangible computer readable storage medium" and "tangible machine readable storage medium" are used interchangeably. Additionally or alternatively, the example processes of FIGS. 5-7 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information. As used herein, the term non-transitory computer readable medium is expressly defined to include any type of computer readable storage device and/or storage disk and to exclude propagating signals and transmission media. As used herein, when the phrase "at least" is used as the transition term in a preamble of a claim, it is open-ended in the same manner as the term "comprising" is open ended.

An example program 500 for measuring and analyzing vibration signatures is illustrated in FIG. 5 and begins at block 502. At block 502, the example pulse generator 300 (FIG. 3) instructs the example ultrasonic transducer 104 (FIGS. 1A-1B) to conduct distance measurements of the example object 108 (FIGS. 1A-1B). The example waveform generator 302 generates a waveform from the data collected by the example ultrasonic transducer 104 (block 504). The example filter 304 resolves the generated waveform to distinguish ultrasonic waves from noise or other interferences (block 506). The example waveform analyzer 306 determines a first vibration characteristic (e.g., frequency (e.g., in Hz), amplitude (e.g., in mm), height (e.g., in mm), velocity (e.g., in mm/s), acceleration (e.g., in mm/s$^2$), etc.) of the example object 108 from the filtered waveform (block 508).

At block 510, the example comparator 308 identifies if a type (e.g., frequency, amplitude, height, velocity, acceleration, etc.) of the first vibration characteristic from block 508 exists in the example characteristic database 312 (e.g., previously measured and stored, downloaded from a network, etc.). If the example comparator 308 identifies the vibration characteristic type is not in the example characteristic database 312 (block 510: NO), then the example signature associator 310 associates an "unknown" identifier (e.g., an indicator that this characteristic has not yet been measured) with the first vibration characteristic (block 512). In the illustrated example, the example "unknown" identifier indicates the example object 108 is displaying the first vibration characteristic for the first time. Control proceeds to block 524.

If the example comparator 308 identifies the vibration characteristic type is in the example characteristic database 312 (block 510: YES), then the example comparator 308 determines if the first vibration characteristic (from block 508) conflicts with a stored characteristic of the same type (e.g., a frequency characteristic for the example object 108 has previously been identified and stored) (block 514). If the example comparator 308 identifies that the first vibration characteristic conflicts with a stored characteristic of the same type (e.g., a first frequency is stored in the example characteristic database 312 and the first vibration characteristic is a second frequency different from the first frequency) (block 514: YES), then the example signature associator 310 associates an "abnormal" identifier (e.g., an indicator that the first vibration characteristic is different from previously identified characteristics) with the first vibration characteristic (block 516). In the illustrated example, the example "abnormal" identifier indicates the example object 108 is operating in an inconsistent manner. Control proceeds to block 524.

The example "abnormal" identifier may indicate the example object 108 is failing, faulty, or going to fail. Alternatively, the abnormal identifier may indicate the example object 108 is turned off. Alternatively, the abnormal identifier may indicate a new signature characteristic of the example object 108 (e.g., a second object causing the example object 108 to act abnormally). In some examples, additional information is added to the example "abnormal" identifier by an operator of the example controller 102 or identified in a definition library of vibration characteristics. For example, when the example signature associator 310 associates an "abnormal" identifier to the first vibration characteristic and the operator knows that the first vibration characteristic is associated with a person's voice reverberating off of the example object 108 (e.g., during a vocal experiment), the operator can manually associate the abnormal identifier with a particular person's voice pattern. Similarly, a person's walking pattern (e.g., a person causes a unique vibration pattern when walking across the example object 108) can be associated with the "abnormal identifier." In this manner, the example characteristic database 312 is filled with unique identification information for people, objects, or the like by associating vibration characteristics with an abnormal identifier unique to the person and/or object. Alternatively, such vibration characteristics (e.g., voice patterns, walking patterns, object interaction patterns, etc.) may be stored in a definition library accessible by the example controller 102.

If the example comparator 308 identifies that the first vibration characteristic does not conflict with a stored characteristic of the same type (block 514: NO), then the example comparator 308 determines if the first vibration characteristic has been measured (e.g., identified, determined, etc.) a threshold amount of times (block 518). The threshold may be set to any threshold such that consistent vibration characteristic patterns emerge. If the example comparator 308 determines that the first vibration characteristic has been measured a threshold amount of times (block 518: YES), then the example signature associator 310 associates a "normal" identifier with the first vibration characteristic (block 520). In the illustrated example, the example "normal" identifier indicates the example object 108 is operating in a consistent manner (e.g., similar vibration characteristics have been measured for the threshold amount of times). Control proceeds to block 524.

In some examples, additional information is added to the example "normal" identifier by an operator of the example controller 102 or is stored in a definition library to further distinguish normal operating conditions. For example, "normal" operation may be associated with particular vibration characteristics (e.g., the example object 108 is normally turned on, the example object 108 has a signature frequency, etc.). In such examples, the "abnormal" identifier would conversely be associated with any vibration characteristic different from the particular vibration characteristics (e.g., the example object 108 that is normally on is now displaying no vibration characteristics (e.g., powered off), the example object 108 is no longer displaying the signature frequency, etc.).

Alternatively, normal operation may be associated with no vibration characteristics at all (e.g., the example object 108 is normally turned off (e.g., inactive), the example object 108 is the ground and has no measurable vibration characteristics under normal conditions, etc.). In such examples, the "abnormal" identifier would conversely be associated with any vibration characteristic (e.g., the example object that is normally off is now displaying vibration characteristics (e.g. powered on), the example object 108 is the ground and vibrating due to people walking on it, an earthquake, other objects contacting or falling onto the example object 108, etc.).

If the example comparator 308 determines that the first vibration characteristic has not been measured a threshold amount of times (block 518: NO), then the example signature associator 310 associates a "known" identifier with the vibration characteristic (block 522). In the illustrated example, the example "known" identifier indicates the example object 108 is redisplaying the first vibration characteristic. However, because the example comparator 308 determined that the first vibration characteristic has not been measured a threshold amount of times, the signature associator 310 increments a count of the number of times the first vibration characteristic has been measured (e.g., increments the number of times the signature associator 310 has handled the first vibration characteristic) (block 526). Control proceeds to block 524.

After the example signature associator 310 associates an identifier (e.g., known (block 522), unknown (block 512), normal (block 520), abnormal (block 516), etc.) with the first vibration characteristic, the example signature associator 310 stores the first vibration characteristic and any associated identifier as a signature characteristic of the example object 108 (block 524).

The example signature associator 310 additionally associates the first vibration characteristic with any additional vibration characteristics associated with the example object 108 that are stored in the example characteristic database 312. For example, the example signature associator 310 aggregates other vibration signature characteristics associated with the example object 108 together to identify the example object 108 by its signature characteristics. The aggregation of signature characteristics make up a signature profile (e.g., consisting of numerous signature characteristics) of the example object 108.

The example waveform analyzer 306 determines if there are additional vibration characteristics of the example object 108 different from the first vibration characteristic (block 528). If the example waveform analyzer 306 identifies additional vibration characteristics (block 528: YES), control returns to block 508. If the example waveform analyzer 306 identifies no additional vibration characteristics (block 528: NO), the example program 500 ceases.

An example program 600 for measuring and analyzing vibration signatures is illustrated in FIG. 6 and begins at block 602. At block 602, the example pulse generator 300 (FIG. 3) instructs the example ultrasonic transducer 104 (FIGS. 1A-1B) to conduct distance measurements of the example object 108 (FIGS. 1A-1B). The example waveform generator 302 generates a waveform from the data collected by the example ultrasonic transducer 104 (block 604). The example filter 304 resolves the generated waveform to distinguish ultrasonic waves from noise or other interferences (block 606). The example waveform analyzer 306 determines a second vibration characteristic (e.g., frequency (e.g., in Hz), amplitude (e.g., in mm), height (e.g., in mm), velocity (e.g., in mm/s), acceleration (e.g., in mm/s$^2$), etc.) of the example object 108 from the filtered waveform (block 608).

At block 610, the example comparator 308 identifies if the second vibration characteristic (e.g., frequency, amplitude, height, velocity, acceleration, etc.) is associated with a signature characteristic stored in the example characteristic database 312 (e.g., previously measured and stored, downloaded from a network, identified in a definition library, etc.). If the example comparator 308 identifies the second vibration characteristic is associated with a signature characteristic stored in the example characteristic database 312 (block 610: YES), then the example reporter 314 reports the signature characteristic and/or any associated identifier (block 612).

For example, the example reporter 312 reports known and/or normal characteristics. Known characteristics include characteristics associated with particular object identities (e.g., voice recognition, walking pattern recognition, and object recognition based on definition libraries, operator input during tests, etc.). Normal characteristics include a particular characteristic or set of characteristics (e.g., a frequency of 29 Hz and an amplitude of 13 mm, a frequency of 0 Hz and an amplitude of 0 mm, etc.) consistently measured by the example methods and apparatus disclosed herein.

If the example comparator 308 identifies the second vibration characteristic is not associated with a signature characteristic stored in the example characteristic database 312 (block 610: NO), then the example reporter 314 generates an alert indicating unknown and/or abnormal characteristics have been identified. Unknown characteristics include characteristics not previously identified or stored in a definition library. Abnormal characteristics include characteristics that conflict with normal characteristics. Thereafter, the example program 600 ceases.

In the illustrated example, the example program 500 and the example program 600 are executed in parallel, such that as the signature associator 310 is determining what identifier to associate with a given characteristics, the example reporter 314 is reporting and/or generating alerts in response to identifier type (e.g., alert for unknown and/or abnormal characteristics, report for known and/or normal characteristics, etc.). Alternatively, the example program 600 may be ran after running the example program 500.

FIG. 7 is a flow chart illustrating an example implementation of blocks 506 and 606. The example implementation of block 506 and 606 starts at block 700. At block 700, the example filter 304 receives a time domain waveform characterizing the example object 108 from the example waveform generator 302. In the illustrated example, the example filter 304 bandpass filters the generated waveform to keep certain frequencies (e.g., within a passband) and exclude other frequencies (block 702). The example filter 304 performs a FIR Hilbert transform on the filtered waveform to shift the phase (block 704). The example filter 304 envelopes the generated waveform (block 706).

In the illustrated example, the example waveform analyzer 306 determines a maximum amplitude of the enveloped waveform (block 708). Thereafter, the example waveform analyzer 306 identifies a first time point related to the generated waveform (block 710). The example waveform analyzer 306 determines if, at the first time point, the envelope amplitude is greater than half of the maximum amplitude (block 712). If the example waveform analyzer 306 determines, at the first time point, that the envelope amplitude is greater than half of the maximum amplitude (block 712: YES), control proceeds to block 714. Otherwise (block 712: NO), control returns to block 710.

At block 714, the example waveform analyzer 306 identifies a threshold amount of additional time points (e.g., 10) surrounding the first time point. Thereafter, the example waveform generator 302 creates a phase domain waveform based on the threshold amount of additional time points and the example waveform analyzer 306 performs linear regression on the threshold amount of additional time points (block 716). The example waveform analyzer 306 identifies a zero-crossing nearest the time point (block 718). At the nearest zero-crossing, the example waveform analyzer identifies the subwavelength resolution of the example object 108 (block 720). Thereafter, the example implementation of blocks 506 and 606 ceases.

Figure 8:
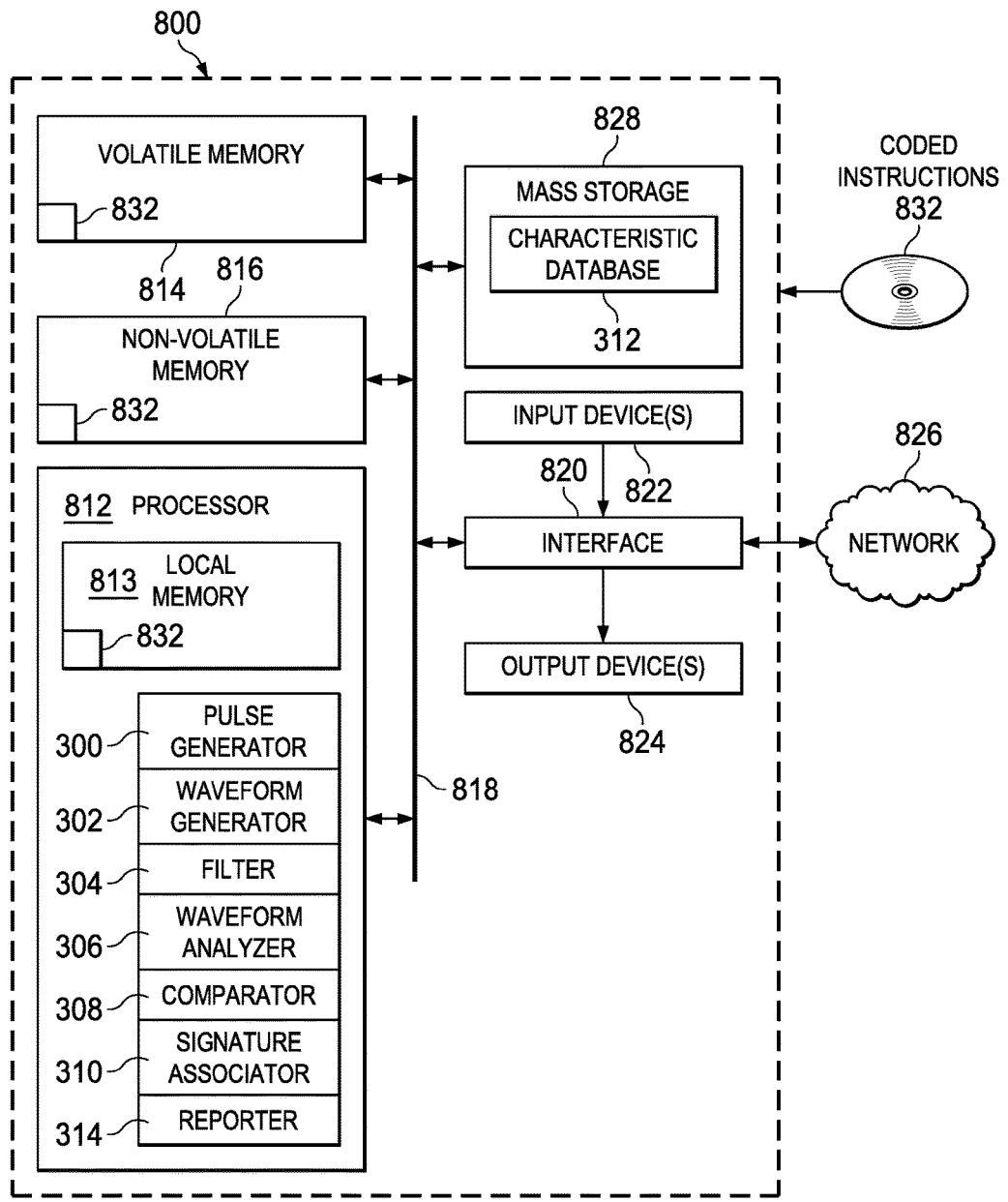
FIG. 8 is a block diagram of an example processor platform to implement the example flow charts of FIGS. 5-7.

FIG. 8 is a block diagram of an example processor platform 800 capable of executing the instructions of FIGS. 5-7 to implement the example controller 102 of FIGS. 1-3. The processor platform 800 can be, for example, a microprocessor, a server, a personal computer, a mobile device (e.g., a cell phone, a smart phone, a tablet such as an iPad™, etc.), a personal digital assistant (PDA), an Internet appliance, or any other type of computing device.

The processor platform 800 of the illustrated example includes a processor 812. The processor 812 of the illustrated example is hardware. For example, the processor 812 can be implemented by one or more integrated circuits, logic circuits, microprocessors or controllers from any desired family or manufacturer.

The processor 812 of the illustrated example includes a local memory 813 (e.g., a cache). The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor 812 further includes the example pulse generator 300, the example waveform generator 302, the example filter 304, the example waveform analyzer 306, the example comparator 308, the example signature associator 310, and the example reporter 314.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a user to enter data and commands into the processor 812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives. The one or more mass storage devices 828 include the example characteristic database 312.

The coded instructions 832 of FIGS. 5-7 may be stored in the mass storage device 828, in the volatile memory 814, in the non-volatile memory 816, and/or on a removable tangible computer readable storage medium such as a CD or DVD.

From the foregoing, it will be appreciate that the disclosed methods, apparatus, and articles of manufacture provide off-device vibration measurement and analysis using ultrasonic transducers to detect subwavelength vibration characteristics. The disclosed methods, apparatus, and articles of manufacture are not subject to the substantial wear, contaminants, moving parts, and volatile environments to which on-device vibration methods and apparatus are subjected, adapt to varying temperatures, and provide increased resolution in the characteristics measured.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A meter, comprising:
   an ultrasonic transducer to generate an emission at a first frequency;
   a waveform generator to generate a waveform representing periodic vibration of an object at a second frequency different from the first frequency based on a first set of distance measurements between the ultrasonic transducer of the meter and the object;
   a waveform analyzer to determine a first vibration characteristic of the object based on the waveform;
   a comparator to compare the first vibration characteristic of the object to a signature vibration characteristic of the object; and
   a reporter to generate an alert, in response to determining that the first vibration characteristic of the object does not match the signature vibration characteristic of the object.

2. The meter of claim 1, wherein the first vibration characteristic is at least one of the second frequency, an amplitude, a height, a velocity, or an acceleration of the periodic vibration.

3. The meter of claim 1, wherein the first set of distance measurements between the ultrasonic transducer and the object are obtained by the ultrasonic transducer using a sampling window having a duration that is inversely proportional to the second frequency of the periodic vibration of the object.

4. The meter of claim 1, wherein the first frequency of the ultrasonic transducer is at least 40 kilohertz.

5. The meter of claim 1, wherein the ultrasonic transducer is a first ultrasonic transducer configured to obtain the first set of distance measurements from a first surface of the object, further including a second ultrasonic transducer in communication with a bus, the second ultrasonic transducer configured to obtain a second set of distance measurements between the second ultrasonic transducer and a second surface of the object.

6. The meter of claim 1, wherein the object is a first object, further including a signature associator to associate the first vibration characteristic with at least one of an abnormal characteristic of the first object, an inactive characteristic of the first object, or a signature vibration characteristic of a second object, the second object causing the first object to present the first vibration characteristic.

7. The meter of claim 1, wherein the object is a first object, the alert is to indicate at least one of an abnormal characteristic of the first object, an inactive characteristic of the first object, a previously undetected characteristic of the first object, or a signature vibration characteristic of a second object, the second object causing the first object to present the first vibration characteristic.

8. The meter of claim 1, further including a signature associator to store the first vibration characteristic as a signature vibration characteristic of a second object, the second object causing the object to present the first vibration characteristic.

9. The meter of claim 1, wherein the comparator is to identify a walking pattern of an individual based on the first vibration characteristic, the first vibration characteristic associated with vibrations caused by the individual walking on the object.

10. The meter of claim 1, wherein the waveform analyzer is to:
    determine a maximum amplitude of the first set of distance measurements;
    determine a time where an amplitude of the waveform is greater than half the maximum amplitude;
    perform phase linear regression on multiple points around the time;
    determine a nearest zero crossing based on the multiple points; and
    determine a sub wavelength resolution based on the nearest zero crossing.

11. The meter of claim 1, wherein the waveform analyzer is to:
    determine an amplitude of the waveform;
    determine a velocity of the waveform based on the amplitude; and
    determine an acceleration of the waveform based on the velocity.

12. The meter of claim 1, wherein the first set of distance measurements is distributed over a plurality of periods of the periodic vibration.

13. The meter of claim 1, wherein the waveform generator is to generate the waveform as a summation of sinusoidal waves.

14. A method, comprising:
    obtaining, via an ultrasonic transducer operating at a first frequency, a first set of distance measurements between the ultrasonic transducer and an object;
    generating, via a processor, a waveform based on the first set of distance measurements representing periodic vibration of the object at a second frequency different from the first frequency;
    determining, via the processor, a first vibration characteristic of the object based on the waveform;
    comparing, via the processor, the first vibration characteristic of the object to a signature vibration characteristic of the object; and
    generating, via the processor, an alert, in response to determining that the first vibration characteristic of the object does not match the signature vibration characteristic of the object.

15. The method of claim 14, wherein the first vibration characteristic is at least one of the second frequency, an amplitude, a height, a velocity, or an acceleration.

16. The method of claim 14, wherein the first set of distance measurements between the ultrasonic transducer and the object are obtained using a sampling window having a duration that is inversely proportional to the second frequency of the periodic vibration of the object.

17. The method of claim 14, wherein the first set of distance measurements are relative to a first surface of the object, further including obtaining a second set of distance measurements between a second ultrasonic transducer and a second surface of the object.

18. The method of claim 14, wherein the object is a first object, further including associating the first vibration characteristic with at least one of an abnormal characteristic of the first object, an inactive characteristic of the first object, or a signature vibration characteristic of a second object, the second object causing the first object to present the first vibration characteristic.

19. The method of claim 14, wherein the object is a first object, the alert indicative of at least one of an abnormal characteristic of the first object, an inactive characteristic of the first object, or a signature vibration characteristic of a second object, the second object causing the first object to present the first vibration characteristic.

20. The method of claim 14, further including storing the first vibration characteristic as a signature vibration characteristic of a second object, the second object causing the object to present the first vibration characteristic.

21. The method of claim 14, further including resolving the waveform by removing noise measured by the ultrasonic transducer.

22. The method of claim 14, further including identifying a walking pattern of an individual based on the first vibration characteristic, the first vibration characteristic associated with vibrations caused by the individual walking on the object.

23. The method of claim 14, further including:
    determining a maximum amplitude of the first set of distance measurements;
    determining a time where an amplitude of the waveform is greater than half the maximum amplitude;
    performing phase linear regression on multiple points around the time;
    determining a nearest zero crossing based on the multiple points; and
    determining a sub wavelength resolution based on the nearest zero crossing.

24. The method of claim 14, further including:
    determining an amplitude of the waveform;
    determining a velocity of the waveform based on the amplitude; and
    determining an acceleration of the waveform based on the velocity.

25. A meter, comprising:
    an ultrasonic transceiver connected to an amplifier circuit, the ultrasonic transceiver to produce a wave at a first frequency to obtain first set of distance measurements between the ultrasonic transceiver and an object and convert the first set of distance measurements into a signal that represents periodic vibration of the object at a second frequency that is different from the first frequency, the amplifier circuit to receive the signal from the ultrasonic transceiver and amplify the signal, to generate an amplified signal;
    a filter circuit connected to the amplifier circuit, the filter circuit to receive the amplified signal from the amplifier circuit and filter the amplified signal, to generate a filtered amplified signal; and
    a controller connected to the filter circuit, the controller to:

analyze the filtered amplified signal from the filter circuit;

determine characteristics of the filtered amplified signal, to generate determined characteristics; and generate an alert, in response to determining that the determined characteristics do not match characteristics stored in a database.

* * * * *